United States Patent [19]

Manger et al.

[11] Patent Number: 5,420,011

[45] Date of Patent: May 30, 1995

[54] CELL BIOASSAY FOR NEUROTOXINS

[75] Inventors: Ronald L. Manger, Edmonds; Linda S. Leja, Lynnwood; Sue Y. Lee, Mill Creek; James M. Hungerford, Bothell; Marleen M. Wekell, Redmond, all of Wash.

[73] Assignee: The United States of America as represented by the Department of Health and Human Services, Washington, D.C.

[21] Appl. No.: 45,067

[22] Filed: Apr. 12, 1993

[51] Int. Cl.$^6$ .......................................... G01N 33/567
[52] U.S. Cl. .................................. 435/7.21; 435/29; 435/948; 435/975; 436/815
[58] Field of Search ...................... 435/7.21, 948, 975, 435/29; 436/501, 815

[56] References Cited

U.S. PATENT DOCUMENTS 5,118,624 6/1992 Parrish et al. .................... 435/240.2

OTHER PUBLICATIONS

Gallacher, et al. A tissue culture assay for direct detection of sodium channel blocking toxins in bacterial culture supernates. FEMS Microbiology Letters 92:101–108, 1992.
James M. Hungerford, *Seaford Toxins and Seafood Products*, 76 General Referee Reports: Journal of AOAC International, 120–28 (1993).
William A. Catterall, *Neurotoxins That Act On Voltage-Sensitive Sodium Channels in Excitable Membranes*, 20 Ann. Rev. Pharmacol. Toxicol., 15–43 (1980).
Charles C. Davis, *Gymnodinium Brevis Sp. Nov., A Cause Of Discolored Water And Animal Mortality in The Gulf of Mexico*, Botanical Gazette, 358–60 (1948).
Karen A. Steidinger & Daniel G. Baden, *Toxic Marine Dinoflagellates*, Dinoflagellates, (1984).
Daniel G. Baden, *Marine Food–Borne Dinoflagellate Toxins*, 82 International Review of Cytology, (1983).
Jean-Noel Bidard et al., *Ciguatoxin Is a Novel Type of Na+ Channel Toxin*, 259 The Journal of Biological Chemistry, 8353–57, (1984).
Kazuhiro Kogure et al., *A Tissue Culture Assay For Tetrodotoxin, Saxitoxin and Related Toxins*, 26 Toxicon, 191–97, (1988).
Joanne F. Jellett et al., *Paralytic Shellfish Poison (Saxitoxin Family) Bioassays: Automated Endpoint Determination and Standardization of the In Vitro Tissue Culture Bioassay, and Comparison with the Standard Mouse Bioassay*, 30 Toxicon, 1143–56, (1992).
Tim Mosman, *Rapid Colorimetric Assay for Cellular Growth and Survival: Application to Proliferation and Cytotoxicity Assays*, 65 Journal of Immunological Methods, 55–63 (1983).
*Paralytic Shellfish Poison: Biological Method, Final Action*, 959.08 AOAC Official Methods of Analysis, 881 (1990).
James Carmichael, *Evaluation of a Tetrazolium-based Semiautomated Colorimetric Assay: Assessment of Chemisensitivity Testing*, 47 Cancer Research, 936–42 (1987).

(List continued on next page.)

*Primary Examiner*—Esther M. Kepplinger
*Assistant Examiner*—Donna C. Wortman
*Attorney, Agent, or Firm*—Foley & Lardner

[57] ABSTRACT

An inventive bioassay method can be used to determine the presence in a fluid sample of a toxin having sodium channel-affecting activity. The method includes the steps of incubating a plurality of cultures of cells which are responsive in a dose-dependent manner to sodium channel-affecting toxins with (i) a medium comprising a solution of ouabain and veratridine and (ii) a portion of the fluid sample, each culture being incubated with a different concentration of the fluid sample; removing the medium and fluid sample from the cultures; incubating the cultures with a medium comprising an indicator which is acted upon by living cells to form a measurable product; measuring the amounts of product formed during the preceding step; and relating the amounts of product measured to a standard calibration curve to determine the presence of the toxin in the sample. The method is readily embodied in kit form and is amenable to automation.

14 Claims, 4 Drawing Sheets

OTHER PUBLICATIONS

William A. Catteral & Martin Risk, *Toxin $T_{46}$ from Ptychodiscus brevis (Formerly Gymnodinium breve) Enhances Activation of Voltage-Sensitive Sodium Channels by Veratridine*, 19 Molecular Pharmacology, 345–48 (1981).

Vladimir Kotnik & W. Robert Fleischmann, Jr., *A simple and rapid method to determine hemotopietic growth factor activity*, 129 Journal of Immunological Methods, 23–30 (1990).

Todd H. Wasserman, M. D. & Peter Twentyman, Ph.D., *Use Of A Colorimetric Microtiter (MTT) Assay In Dermining The Radiosensitivity of Cells From Murine Solid Tumors*, 15 Int. J. Radiation Oncology Biol. Phys., 699–702 (1988).

Michael C. Alley et al., *Feasibility of Drug Screening with Panels of Human Tumor Cell Lines Using a Microculture Tetrazolium Assay*, 48 Cancer Research, 589–601 (1988).

J. W. Pearson et al., *Combined drug and immunotoxin therapy against a human colon tumor xenografted into nude mice*, 30 Proceedings of the American Association for Cancer Research, (1989).

Ron Manger et al., *Detection of Ciguatoxin, Brevetoxin, and Saxitroxin by Cell Bioassay*, Ciguatera Meeting, Australia, (1993).

Hungerford et al., "Analytical Methods for Marine Toxins," in *Handbook of Natural Toxins*, vol. 7, Food Poisoning, Tu, ed., pp. 416–473, Marcel Decker, Inc., New York (1992).

Catterall, "The Voltage Sensitive Sodium Channel: A Receptor For Multiple Neurotoxins," *In Toxic Dinoflagellates*, Anderson et al., eds., pp. 329–342, Elsevier, New York (1985).

Yasumoto et al., "A Survey of Comparative Toxicity in the Food Chain of Ciguatera," *Bull. Jap. Soc. Sci. Fish.* 43 (8): 1015–1019 (1977).

Gupta et al., Cellular Basis for the Species Differences in Sensitivity to Cardiac Glycosides (Digitalis), Journal of Cellular Physiology 127:197–206, 1966.

Scudiero et al. "Evaluation of a Soluble Tetrazolium/-Formazan Assay for Cell Growth and Drug Sensitivity in Culture Using Human And Other Tumor Cell Lines" *Cancer Res.* 48: 4827–4833 (1988).

Paull et al. "The Synthesis of XTT" *J. Heterocyclic Chem.* 25: 911–913 (1988).

ABSORBANCE (570 nm) vs CIGUATOXIC EXTRACT (ug)

CELL BIOASSAY FOR NEUROTOXINS

BACKGROUND OF THE INVENTION

The present invention relates to an assay for the detection of sodium channel-specific toxins, particularly marine toxins, based upon mitochondrial dehydrogenase activity in the presence of ouabain and veratridine. More specifically, the present invention concerns a cell bioassay that allows the detection of either sodium channel blocking agents, such as saxitoxin, or sodium channel enhancers like brevetoxin and ciguatoxin.

Commercially important species of shellfish and finfish are known to occasionally present a serious health risk to consumers due to the presence of accumulated marine toxins. A significant number of these marine toxins exert their effects by interaction with voltage sensitive sodium channels in excitable membranes. Paralytic shellfish poisoning (PSP) is attributed to the ingestion of molluscan shellfish that have accumulated saxitoxins or related compounds from toxic dinoflagellate blooms. The saxitoxins selectively block ion transport at the sodium channel. Neurotoxic shellfish poisoning (NSP) is caused by the ingestion of shellfish that have sequestered brevetoxins from the dinoflagellate associated with Florida's red tide. In contrast to the action of saxitoxin, brevetoxins perturb normal membrane properties of excitable cells by activating sodium channels. Ciguatoxins, which accumulate in tropical fish, also exert their biological effects through activation of sodium channels.

Monitoring programs for marine toxins have depended in large part upon mouse bioassays. Although mouse bioassays have for many years provided a fairly reliable assessment of risk, there is mounting pressure to develop alternative assays to reduce the reliance on animal testing. To this end Kogure et al. developed a tissue culture assay for tetrodotoxin, saxitoxin, and related toxins. See Kogure et al., Toxicon 26 (2): 191–97 (1988). In the Kogure assay, a mouse neuroblastoma cell line (Neuro-2a) is treated with a fixed concentration of the sodium channel activator veratridine in the presence of ouabain, an inhibitor of Na+/K+ ATPase. The combined effect of these agents is an enhanced sodium influx, leading to altered cell morphology, a subsequent decrease in cell viability and ultimate cell lysis. Tetrodotoxin, saxitoxin and related toxins which block sodium channels antagonize this effect, essentially rescuing the cells in a dose dependent manner. This phenomenon provides the basis of a sensitive in vitro bioassay for these toxins. But evaluation of the Kogure assay requires the visual scoring of 200 or more cells per sample or well, a potentially time-consuming and operator dependent task.

Scoring of this assay was improved by the modifications described by Jellett et al., Toxicon 30 (10): 1143–56 (1992), the contents of which are hereby incorporated by reference. Jellett et al. used a microplate reader for automated determinations of absorbances of toxin-treated cells which were stained with crystal violet. This assay exploits the difference in adherence to the culture well of cells treated only with ouabain/veratridine and PSP toxin-treated cells. The former cells exhibit diminished adherence to the culture well, associated with swelling and lysis, and thus are readily removed by rinsing, whereas the latter retain substrate adherence. Thus, cells affected only by ouabain/veratridine lose adherence and are removed during rinsing, while cells inoculated with the toxin, and thus protected from the effects of ouabain/veratridine, remain in the well.

In the Jellett assay, wells containing Neuro-2a cells are inoculated with toxin and then with ouabain/veratridine, incubated, and subsequently rinsed. After rinsing, the wells are fixed and subsequently stained with crystal violet. The processed plates are then dried, followed by digestion of the stained cells in acetic acid. Finally, the plates are read for absorbance of crystal violet in each well, with the absorbance being directly related to the amount of PSP toxin originally present. These modifications notably improve the application of the cell bioassay developed by Kogure et al. But the numerous steps involving mechanical removal of cells and treatment of the plates may be subject to operator variability.

Thus, a simplified bioassay for detecting the above-described toxins would be very useful. It also would be desirable to have a bioassay for detecting other types of toxins, especially those marine toxins that are sodium channel activators like the brevetoxins and the ciguatoxins. Since the known tissue culture-based bioassays are limited to detection of sodium channel blocking agents, there is a real need for a tissue culture-based bioassay which can detect marine toxins which have sodium channel activating properties as well display sodium channel blocking activity.

SUMMARY OF THE INVENTION

Accordingly, it is an object of the present invention to provide an improved cell bioassay for sodium channel-affecting toxins, particularly marine toxins.

Another object of the present invention is to provide a cell bioassay capable of detecting both sodium channel-blocking and sodium channel-activating marine toxins.

A further object of the present invention is to provide a simplified cell bioassay.

Yet another object of the present invention is to provide a kit for carrying out the improved cell bioassay.

In accomplishing the foregoing objectives, there has been provided, in accordance with one aspect of the present invention, a cell bioassay method for determining the presence in a fluid sample of a toxin having sodium channel-affecting activity which comprises the steps of: incubating a plurality of cultures of cells which are responsive in a dose-dependent manner to sodium channel-affecting toxins with (i) a medium comprising a solution of ouabain and veratridine and (ii) a portion of the fluid sample, each culture being incubated with a different concentration of the fluid sample; removing the medium and fluid sample from the cultures; incubating the cultures with a medium comprising an indicator which is acted upon by living cells to form a measurable product; measuring the amounts of product formed during the preceding step; and relating the amounts of product so formed during the indicator incubation step to a standard calibration curve to determine the presence of toxin in the sample.

In a preferred embodiment, the cells are mouse neuroblastoma cells of the cell line Neuro-2a (ATCC CCL 131). Preferably, the indicator is 3-(4,5-dimethylthiazol-2-yl)-2,5-diphenyl tetrazolium bromide (MTT), which is metabolized by living cells to yield formazan as the measurable product.

In accordance with another aspect of the present invention there is provided a kit for use in the foregoing cell bioassay method which comprises, in packaged combination: a solution of about 0.5 mM ouabain and about 0.05mM veratridine, a solution of MTT, and means for contacting the solutions with the fluid sample. In a preferred embodiment, the kit also includes a quantity of cells, preferably Neuro-2a cells.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The present invention is more readily understood by reference to the accompanying drawing by which

DETAILED DESCRIPTION OF PREFERRED EMBODIMENTS

The cell bioassay according to the present invention represents a significant improvement over the known assay methods. The inventive bioassay is simpler, faster and more sensitive than the standard mouse assay, and requires less sample than the mouse assay. Furthermore, the instant bioassay can also be carried out more easily than other previously known methods, since it requires fewer steps and no intermediate washing or fixation steps.

It is contemplated that a bioassay according to the invention has utility in determining the presence, not only of marine toxins, but also of any other sodium channel-affecting toxins. (As used herein, the term "sodium channel-affecting activity" denotes both sodium channel-blocking activity and sodium channel-enhancing activity). Exemplary toxins whose presence can be determined by use of bioassays within the invention include: carbamate toxins such as saxitoxin (STX), neosaxitoxin (NEO), gonyautoxins (GTX-I, GTX-II, GTX-III, GTX-IV); other members of the saxitoxin, neosaxitoxin and gonyautoxin families such as decarbamoyl (dc) toxins, including dc-STX, dc-NEO, dc-GTX-I, etc.; N-sulfocaramoyl toxins such as toxins B-1, B-2, C-1, C-2, C-3 and C-4; tetrodotoxins; other PSP-producing toxins; NSP toxins including brevetoxins such as PbTx-1, PbTx-2, PbTx-3, PbTx-5, PbTx-6, PbTx-7, PbTx-8, etc.; ciguatoxins such as CTX-1, CTX-2, CTX-3, etc.; other NSP-producing toxins; and the like (see J. Hungerford et al., "*Analytical Methods for Marine Toxins*", 7 *Food Poisoning: Handbook of Natural Toxins*, ch. 16, pp. 415–473 (ed. A. Tu, Marcel Dekker Inc, New York, N.Y. 1992).

Unlike conventional assay methods, a bioassay within the present invention is effective in determining the presence of toxins having sodium channel-activating (or enhancing) activity, as well as sodium channel-blocking activity. The inventive bioassay thus has additional utility as a diagnostic tool for determining either blocking or enhancing activity at the level of the sodium channel. Specifically, reduction of cytotoxicity in the presence of ouabain/veratridine ("cell rescue") is indicative of a sodium channel blocking toxin, such as saxitoxin or tetrodotoxin; enhancement of cytotoxicity in the presence of ouabain/veratridine is indicative of a potent sodium channel enhancer, such as a brevetoxin or ciguatoxin; while ouabain/veratridine-independent cytotoxicity suggests the presence of a toxin other than a sodium channel-affecting toxin, such as a diarrhetic shellfish poisoning (DSP) toxin, e.g., okadaic acid.

The cell cultures employed according to the inventive bioassay are responsive in a dose-dependent manner to sodium channel-affecting toxins. The dose-dependent response of the cells occurs in the context of prior exposure to ouabain/veratridine. The cells should be readily cultured, and should begin to show such a response within a reasonable time, such as about 4 to 18 hours, in the case of sodium channel-activating toxins, or about 24 to 48 hours in the case of sodium channel-blocking toxins. Preferred cells include mouse neuroblastoma cells of the cell line Neuro-2a (ATCC CCL 131). The cells must also be responsive to the selected indicator.

The indicator employed in a bioassay within the instant invention distinguishes active, living cells from dead cells, and is a substrate for mitochondrial dehydrogenase. Living cells thus act upon the indicator to produce a measurable product, while dead cells do not act upon the indicator to produce a measurable product. A particularly preferred indicator is MTT (3-(4,5-dimethylthiazol-2-yl)-2,5-diphenyl tetrazolium bromide). Other indicator of mitochondrial dehydrogenase activity such as XTT, methylene blue and similar salts can also be used.

Incorporation of the MTT colorimetric test of cellular metabolism enables simplification of the bioassay method with respect to the known methods. The MTT test is a rapid, versatile, quantitative, and simple technique to assess cell proliferation and cytotoxicity based upon the metabolism of MTT by mitochondrial dehydrogenase activity in viable cells. See Mosman, *J. Immuno. Meth.* 65: 55–63 (1983), the contents of which are hereby incorporated by reference. MTT is metabolized only in living cells, whose mitochondria cleave its tetrazolium ring to produce a blue colored product (formazan). The presence of formazan can be detected visually or spectrophotometrically and directly related to the number of living cells.

Thus, the presence of toxins in the fluid sample is determined from the effect of the fluid sample on cell viability, as evidenced by the level of cell metabolism of MTT and resultant formazan production. Increased formazan production upon contact with increasing concentrations of toxin from the fluid sample indicates cell rescue, and hence the presence of sodium channel-blocking toxins. Decreased formazan production, on the other hand, indicates the presence of sodium channel-activating toxins.

Besides MTT, it is contemplated that other indicators which are similarly capable of distinguishing living from dead cells can be employed in bioassays within the instant invention. One such indicator is 2,3-bis(2-methoxy-4-nitro-5-sulfophenyl)-2H-tetrazolium-5-carboxanilide inner salt (XTT) (Sigma #X4251). See Parsons et al., *J. Heterocyclic Chem.* 25:911 (1988); Scudievo et al., *Cancer Res.* 48:4827 (1988).

As noted, no intermediate washing or fixing steps are required in the inventive bioassay method. The cultured cells need only be contacted sequentially with the various fluids, the last being a solvent for formazan which facilitates the spectrophotometric measurement of the amount of formazan produced by the cell culture.

In addition to simplicity, the inventive cell bioassay offers the advantage of significantly improved sensitivity in comparison to the standard mouse bioassay. The animal assay can detect saxitoxin to a lower limit of 40 $\mu g/100$ g tissue See Hungerford et al., 7 HANDBOOK OF NATURAL TOXINS, 416–73, Marcel Dekkar, Inc. (New York 1992). In contrast, the cell bioassay according to the present invention can routinely detect purified saxitoxin at a level of 0.1 ng/10 μl which is the equivalent of 2 μg/100 g tissue. Under some conditions, with extended MTT development time, the observed limit of detection can be reduced to as low as 0.02 ng/10 μl (0.4 μg/100 g). This sensitivity is comparable to that obtained by Jellett et al., supra. The inventive cell assay also shows excellent correlation with the results obtained with the standard mouse bioassay for saxitoxin.

In a similar manner, the instant cell bioassay is more sensitive to the presence of brevetoxins and ciguatoxins than the mouse bioassay. The $LD_{50}$ for brevetoxins in mice is 0.01 mg/20 g animal, i.p. injection. See Hungerford et al., supra. This correlates to 0.1 mg/100 g tissue extract and is the equivalent of a 1 ng/10 μl sample in the instant cell bioassay. In the examples given below, brevetoxins are detected at levels of 0.25 ng/10 μl (Example 4; also FIGS. 4*a*–*b*).

Ciguatoxic extracts (utilized in Example 5, below) produced death in 20 g mice following injection of 50 mg in 1 ml within 2.5 hours (estimated toxicity score of about 0.3 mouse units per mg; bioassay results and sample generously provided by Dr. Yoshitsugi Hokama, University of Hawaii), and contained the estimated equivalent of 100 ng ciguatoxin (CTX-1). The sodium channel activity of this extract was readily detected in the instant cell bioassay at levels of less than $10^{-4}$ mouse units, corresponding to approximately 1 pg of CTX-1.

A significant advantage of the inventive cell bioassay is the rapidity of the method for the detection of sodium channel-activating toxins, such as brevetoxins and ciguatoxins, in comparison to the mouse bioassay. Mouse bioassays for brevetoxins and ciguatoxins involve long observation periods, ranging from several hours to 24 hours. See Hungerford et al., supra. The bioassay according to the invention typically can be effected within 4 to 6 hours of exposure to these toxins, with subsequent processing and development time taking only about 30 minutes.

Although the inventive method typically requires on the order of 24–48 hours for the determination of sodium channel blocking agents such as saxitoxin, such times are also typical of known cell-based assays. Particularly when the rapidity of the mouse bioassay is not required, however, such as in the analysis of embargoed shellfish or in research applications where small aliquots of isolates must be tested, the instant invention offers clear advantages as described above.

For convenience, kits can be provided for carrying out the inventive bioassay method. The kits include the solutions utilized in the method of the invention, with all constituents in appropriate containers (vials, syringes, etc.) in predetermined proportions and amounts. The kits also include means for contacting the solutions with the fluid sample, such as multi-well plates. The kits in addition preferably include an appropriate solvent for formazan, such as DMSO, and at least one calibration curve for a toxin having sodium channel-affecting activity. Cell cultures employed in the bioassay can also be provided with the kits according to an embodiment of the invention. In some instances, such as the preferred embodiments using Neuro-2a cells, it may be necessary to provide the cells and the remaining components of the kits separately, maintained at different temperatures. In another embodiment, the multiwell plates can be "pre-seeded" with the cell culture in a manner known to those skilled in the art, then shipped for overnight delivery to the user with the other kit components.

The inventive bioassay also is well-suited to automation, making possible the screening of large numbers of samples with minimal operator intervention. This provides for a convenient biological assay that can be accomplished within one day.

The present invention is described further by reference to the following, non-limiting examples.

EXAMPLE 1

Cell Culture

The metabolism of MTT has been reported to be minimal in some cell cultures. See, e.g., Carmichael et al., *Cancer Res.* 47: 936–42 (1987); Alley et al., loc. cit. 48: 589–601 (1988)). As shown below, the Neuro-2a cell line has been determined to be capable of effectively metabolizing MTT for the purposes of the inventive bioassay method.

Mouse neuroblastoma cells Neuro-2a (ATCC, CCL 131) were grown and maintained in RPMI 1640 (Sigma) containing 10% fetal bovine serum (Gibco), glutamine (2 mM) (Sigma), and sodium pyruvate (1 mM) (Sigma). Streptomycin and penicillin (Sigma) were also added at 50 μg and 50 units per ml, respectively, to form a growth medium (hereinafter "complete growth medium"). Cultures were maintained in an incubator at 37° C. with a humidified 5% $CO_2$:95% air atmosphere.

The ability of Neuro-2a cells to metabolize this tetrazolium salt as an index of viable cell number is show in FIG. 1. Cells were plated at the density indicated on the x-axis and allowed to recover for 24 hours at 37° C. prior to incubation with MTT for 15 minutes. Following solubilization in an appropriate solvent (here, DMSO), the amount of blue formazan product was then measured at 570 nm. Values shown in FIG. 1 represent the mean of 6 replicates, with the error bars indicating ±SD (standard deviation). Absorbance was proportional to initial cell inoculum and exhibited excellent reproducibility between replicate wells.

EXAMPLE 2

Saxitoxin Cell Bioassay

Purified saxitoxin, obtained from Calbiochem, was diluted in phosphate-buffered saline (PBS), pH 7.4 and maintained as a frozen stock at −20° C. Prior to assay the saxitoxin stock was diluted to the appropriate concentration with complete growth medium.

Cultures were prepared for bioassay as described by Jellett et al., supra, with the modifications described below. Cells were harvested with a trypsin EDTA solution (0.5%/0.2%) (Sigma) in PBS and seeded into 96-well plates (CoStar) at a density of $5 \times 10^5$ cells/ml in 200 μl complete growth medium per well. The cultures were incubated at 37° C. under a 5% $CO_2$ atmosphere for approximately 24 hours before proceeding further.

The culture wells received 10 μl of sample and 10 μl additions of aqueous stocks of 10 mM ouabain (Sigma) and 1 mM veratridine (Sigma), pH 2. Each sample concentration was tested in replicate (3 to 5 wells). A minimum of 15 wells per plate were processed as ouabain/veratridine-treated controls (no sample addition, 0.5 mM ouabain, 0.05 mM veratridine), and a minimum of 5 wells served as untreated controls (without ouabain/veratridine and without sample). Control wells received added culture medium to make up for volume differences of sample and ouabain/veratridine (up to 30 μl per well). The cultures were then incubated for 24-48 hours.

MTT (3-(4,5-dimethylthiazol-2-yl)-2,5-diphenyltetrazolium bromide (Sigma)), was prepared as a 5 mg/ml stock solution in PBS, pH 7.4, and stored at 4° C. until use. Following incubation with the samples, the overlaying medium was removed from each of the cultures, and, without a wash step, 60 μl of a 1:6 dilution of the MTT stock in complete growth medium was added to each well. The cultures were then incubated for approximately 15 minutes at 37° C., or until a suitable deposit of reduced dark formazan deposit was observed in control wells (occasionally up to 30-45 minutes). The incubation medium was then removed, and without, an intermediate rinsing step, 100 μl of DMSO was added to each well. The plates were immediately read on a Dynatech MR-5000 automated multiwell scanning spectrophotometer using a test wavelength of 570 nm and a reference wavelength of 630 nm.

Morphological alteration and subsequent cell loss was observed in cells incubated with 0.5 mM ouabain and 0.05 mM veratridine. This effect was maximal between 24-48 h, in agreement with previous reports. See Kogure et al. and Jellett et al., supra. Saxitoxin-dependent cell rescue was measured directly by alterations in MTT metabolism, as shown in FIG. 2 (values represent the mean of 3-4 replicates).

Figure 1:
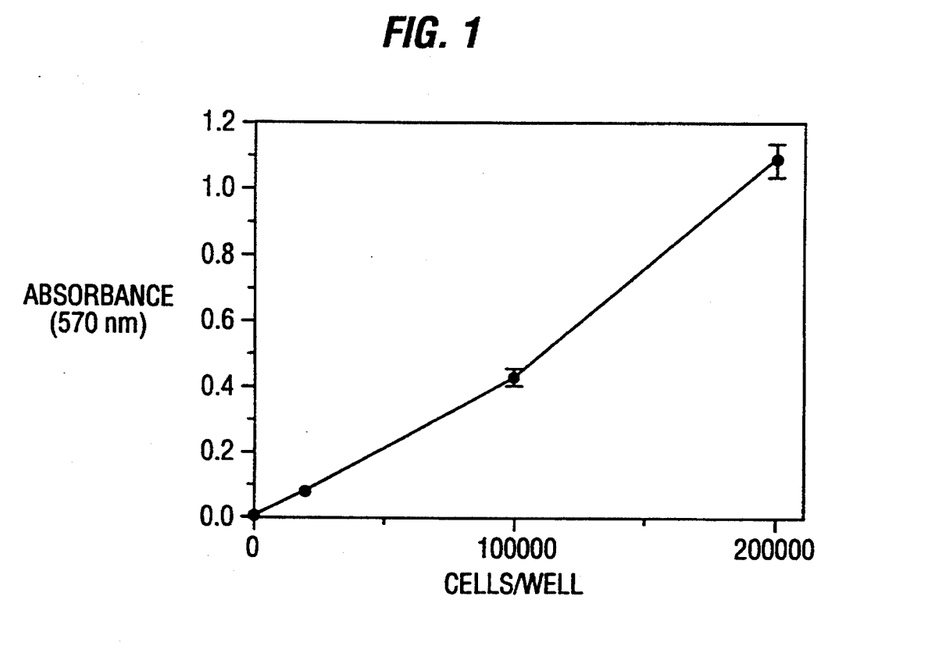
FIG. 1 is a graph of absorbance as a function of cell number in an inventive bioassay.
Figure 2A:
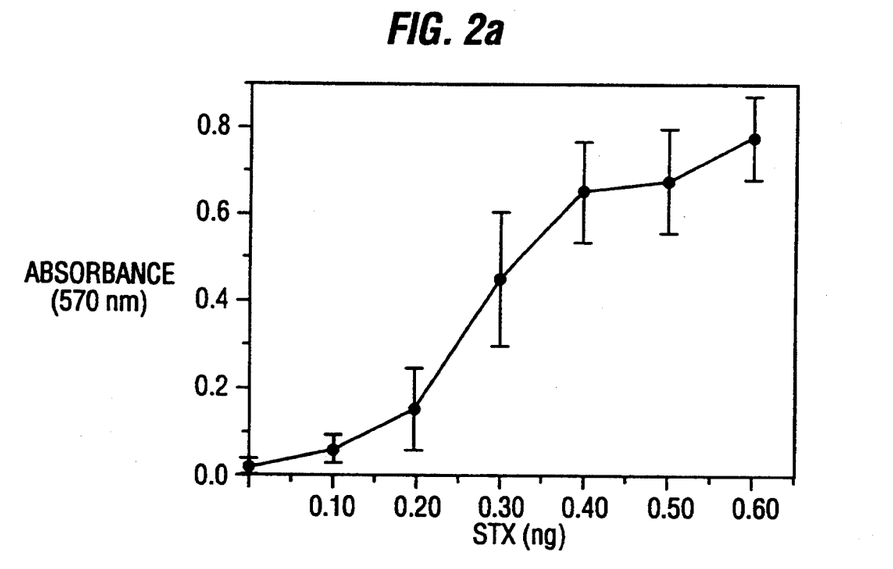
FIG. 2A and 2B are a graph of the effect of increasing concentration of pure saxitoxin upon MTT development in a bioassay of the present invention.
Figure 2B:
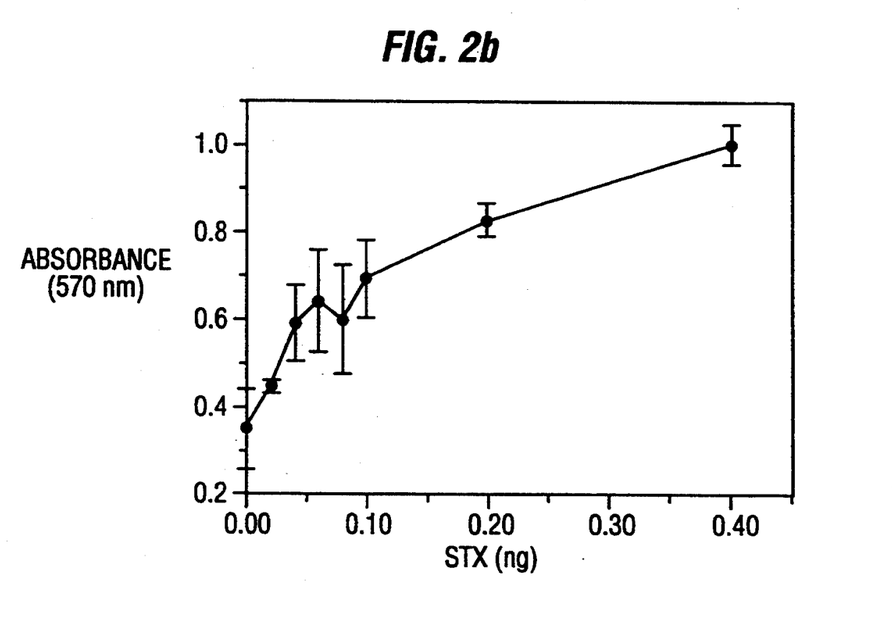

Purified saxitoxin was detected at a level of 0.1 ng/10 μl addition using an approximate MTT development time of 15 minutes (see FIG. 2a). Assay sensitivity could occasionally be enhanced by increasing MTT development time to approximately 45 minutes, with a resultant detection limit of about 0.02 ng/10 μl addition (see FIG. 2b). However, with added MTT development time the assay tended to plateau at higher concentrations of saxitoxin. Assay sensitivities were comparable to that reported by Jellett et al., supra. In the absence of ouabain/veratridine treatment, saxitoxin at the concentrations tested had no measurable effect. (For the purpose of comparison, 0.1 ng/10 μl and 0.02 ng/10 μl saxitoxin are equivalent to shellfish extracts of 2 μg/100 g tissue and 0.4 μg/100 g tissue, respectively.)

EXAMPLE 3

Cell Bioassay of Crab Viscera

To test the applicability of the inventive bioassay for the detection of naturally incurred PSP in samples, acid extracts of viscera from Dungeness crab, *Cancer magister*, were examined. The crab viscera extracts were generously made available by Cheryl Eklund and James Bryant, FDA, Bothell, Washington. Toxicity levels were determined previously by mouse bioassay of the entire visceral portions of the crabs. See OFFICIAL METHODS OF ANALYSIS OF THE AOAC, par. 959.08, 881 (K. Helrich, ed. 1990).

Two extracts exhibiting positive and negative PSP activity by the AOAC mouse bioassay (122 μg/100 g and none detected/100 g respectively) were tested at various dilutions in the cell bioassay. Cultures were prepared for bioassay, incubated and assayed as described in Example 2.

Figure 3:
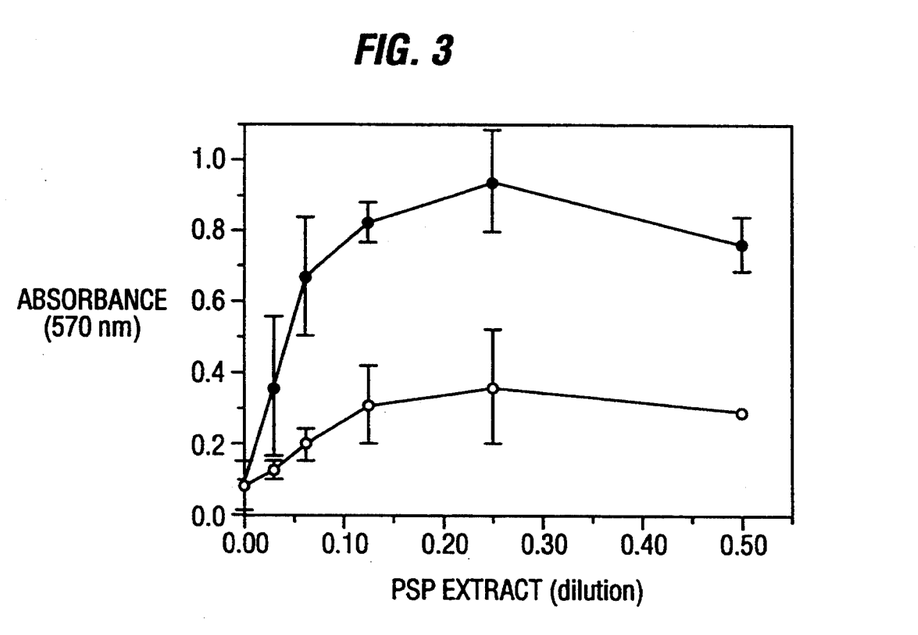
FIG. 3 is a graph of PSP toxin activity in aqueous Dungeness crab extracts as determined by an inventive bioassay.

Levels of saxitoxin activity were calculated by comparing linear portions of the crab viscera dose response curves (dilutions of 1/32, 1/16, and ⅛) with a standard curve derived using pure saxitoxin, and multiplying interpolated toxin concentrations by the appropriate dilution factor. Results are set forth in FIG. 3, in which (●) and (○) indicate extracts testing at 122 μg/100 g and no detectable activity using the standard mouse bioassay, respectively.

As calculated from the three highest dilutions, the cell bioassay detected mean values (with standard deviations) of 124±44 μg/100 g in the positive extract (mouse bioassay). Interestingly, the extract that was PSP-negative by mouse bioassay had a mean value of 33±2 μg/100 g tissue in the inventive bioassay. This level of saxitoxin is below the standard detection limit of the animal test (40 μg/100 g).

The dose response curves tended to plateau with increasing concentrations of extract (dilutions of less than 1:4), suggesting a competing or potentially interfering cytotoxic component.

EXAMPLE 4

Brevetoxin Cell Bioassay

Brevetoxins PbTx-1 and PbTx-3 (Calbiochem) were dissolved in methanol to form a stock. Prior to assay brevetoxin stock solution was diluted 1:100 in complete growth medium, from which serial dilutions in complete growth medium were then made.

The cultures were prepared for bioassay as described in Example 2, except that 10 μl samples were added to replicate culture wells in both the presence and absence of ouabain and veratridine. The cultures were then incubated 2-22 hours.

Figure 4A:
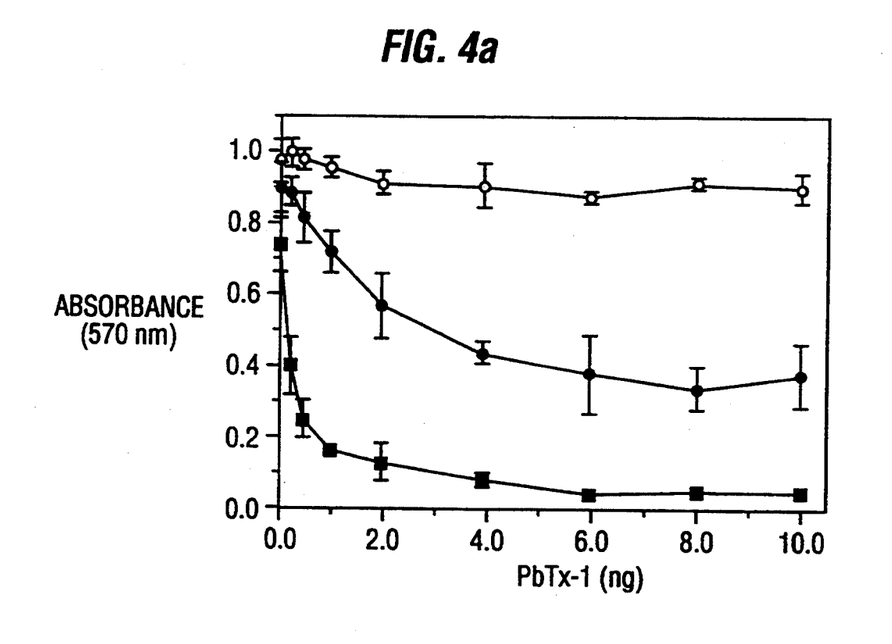
FIG. 4A and 4B are a graph of brevitoxin PbTx-1 cytotoxicity as measured by an inventive assay.
Figure 4B:
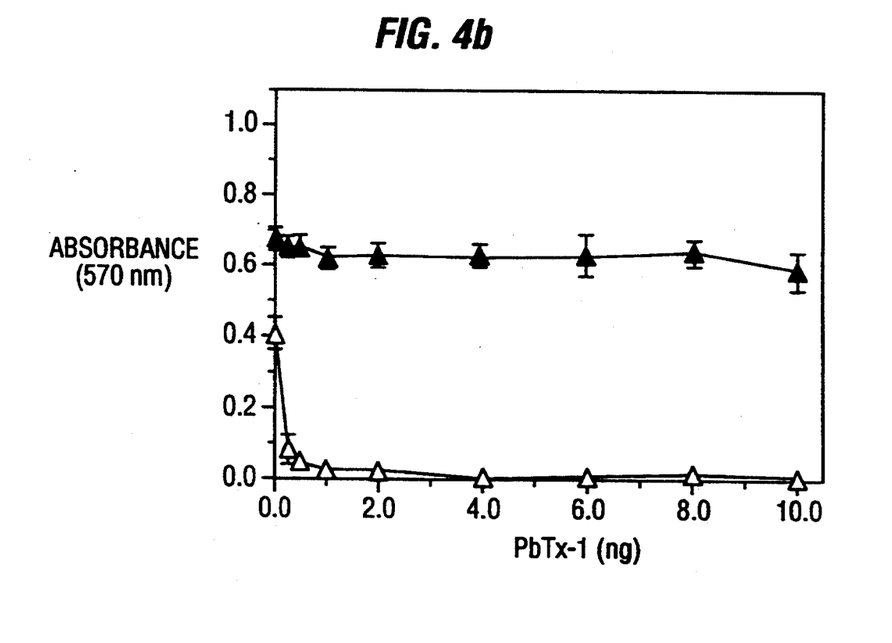

The cell bioassay was performed essentially as described in Example 2 for saxitoxin. However, instead of measuring cell rescue, an assessment of toxin-enhanced cytotoxicity in the presence of ouabain/veratridine was performed. The effect of increasing concentrations, and time of exposure, of brevetoxin PbTx-1 in the cell bioassay are shown in FIGS. 4a and b. In the figures, brevetoxin cytotoxicity was assayed at 2 hours (○), 4 hours (●), 6 hours (■) and 18 hours (Δ). Values represent the mean of four replicates.

In the dose range explored, titratable cytotoxicity was observed as early as 4 hours (FIG. 4a) and was essentially total at 18 hours. Brevetoxin in the absence of ouabain/veratridine was not cytotoxic even at the highest concentration and incubation time tested (10 ng/10 μl, 18 hours exposure) (FIG. 4b). PbTx-3 produced similar results as observed for PbTx-1 in the cell bioassay.

EXAMPLE 5

Ciguatoxin Cell Bioassay

A ciguatoxic fish extract (methanol fraction), prepared from wrasse, *Cheilinus rhodochrous*, was generously provided by Dr. Yoshitsugi Hokama, University of Hawaii. A stock solution of this material was prepared in the same manner as the brevetoxins in Example 4.

Figure 5:
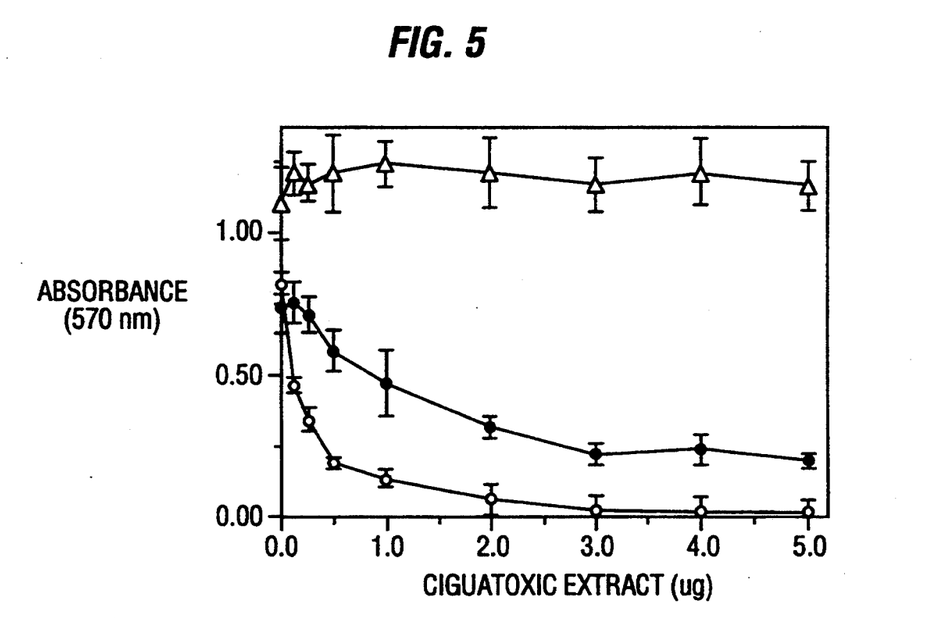
FIG. 5 is a graph of ciguatoxin activity in wrasse extracts, as determined by an assay within the present invention.

Cultures were prepared for bioassay, incubated and assayed as described in Example 4. The extract was diluted and applied to the cells in the presence or absence of ouabain/veratridine. Within 6 hours the sample produced significant dose-dependent cytotoxicity only in cells treated with ouabain/veratridine (data obtained at 6 hours (●) and 22 hours (○)), as shown in FIG. 5 (values represent the mean of four replicates). Even after prolonged exposures of up to 22 hours the ciguatoxic extract was not cytotoxic in the inventive cell bioassay in the absence of ouabain/veratridine treatment (data obtained at 22 hours (Δ)).

EXAMPLE 6

Kit

The following components are combined in packaged form (liquid solutions in appropriate containers):

| | |
|---|---|
| ouabain/veratridine solution (0.5 mM/0.05 mM) | 5–25 ml |
| MTT solution (5 mg/ml in PBS, pH 7.4) | 5–25 ml |
| 96-well plate (1) | |

What is claimed is:

1. A cell bioassay method for determining the presence in a fluid sample of a toxin having sodium channel-activating activity which comprises the steps of
   (a) incubating a plurality of cultures of mouse neuroblastoma cells which are responsive in a dose-dependent manner to sodium channel-activating toxins with (i) a medium comprising a solution of ouabain and veratridine and (ii) a portion of said fluid sample, each said culture being incubated with a different concentration of said fluid sample,
   (b) removing said medium and fluid sample from said cultures,
   (c) incubating said cultures with a medium comprising an indicator which is acted upon by living cells to form a measurable product,
   (d) measuring the amounts of product formed during step (c), and
   (e) relating the amounts of product measured in step (d) to a standard calibration curve to determine the presence of said toxin in said sample.

2. A method as claimed in claim 1, wherein said mouse neuroblastoma cells are of the cell line Neuro-2a (ATCC CCL 131).

3. A method as claimed in claim 1, wherein said indicator is 3-(4,5-dimethylthiazol-2-yl)-2,5-diphenyl tetrazolium bromide (MTT) and said measurable product is formazan.

4. A method as claimed in claim 1, wherein in step (a) said cultures are incubated with about 0.5 mM ouabain and about 0.05 mM veratridine.

5. A method as claimed in claim 1, wherein step (a) is carried out for about 2 to 22 hours.

6. A method as claimed in claim 5, wherein step (a) is carried out for about 4 to 6 hours.

7. A method as claimed in claim 1, wherein said toxin is an neurotoxic shellfish poisoning (NSP) toxin.

8. A method as claimed in claim 7, wherein said toxin is a brevetoxin.

9. A method as claimed in claim 1, wherein said toxin is a ciguatoxin.

10. A method as claimed in claim 1, wherein step (d) is effected by colorimetric means.

11. A method as claimed in claim 1, wherein said indicator is XTT.

12. A method as claimed in claim 1, wherein said indicator is methylene blue.

13. A cell bioassay method for determining the sodium channel effect of a toxin in a fluid sample, which method comprises the steps of
   (a) incubating a plurality of cultures of mouse neuroblastoma cells which are responsive in a dose-dependent manner to sodium channel-affecting toxins with (i) a medium comprising a solution of ouabain and veratridine and (ii) a portion of said fluid sample, each said culture being incubated with a different concentration of said fluid sample,
   (b) removing said medium and fluid sample from said cultures,
   (c) incubating said cultures with a medium comprising an indicator which is acted upon by living cells to form a measurable product,
   (d) measuring the amounts of product formed during step (c), and
   (e) relating the amounts of product measured in step (d) to a standard calibration curve to determine the sodium channel effect of said toxin, wherein the presence of a sodium channel-blocking toxin is indicated by an increase in the amount of product measured in step (d) as said concentration of said fluid sample increases and the presence of a sodium channel activating toxin is indicated by a decrease in the amount of product measured in step (d) as said concentration of said fluid sample increases.

14. A process according to claim 13, further comprising the steps of
   (f) incubating a culture of said mouse neuroblastoma cells with a portion of said fluid sample,
   (g) removing said fluid sample from said culture,
   (h) incubating said culture with said medium comprising said indicator,
   (i) measuring the amount of product formed during step (h), and
   (j) relating the amounts of product measured in step (d) to the amount of product measured in step (i) to determine the ouabain/veratridine dependence of the amount of product formed, wherein an ouabain/veratridine dependence of the amount of product formed indicates the presence of a sodium channel-affecting toxin, and an ouabain/veratridine independence of the amount of product formed indicates the presence of a toxin that is not sodium channel-affecting.

* * * * *